United States Patent [19]
Avila et al.

[11] Patent Number: 5,308,331
[45] Date of Patent: May 3, 1994

[54] SINGLE USE SYRINGE

[76] Inventors: Les Avila, 170 Oakmount Rd., Toronto, Ontario, Canada, M6P 2M9; Samir Machhour, P.H. 11, 284 Mill Road, Etobicoke, Ontario, Canada, M9C 4W6

[21] Appl. No.: 998,608

[22] Filed: Dec. 30, 1992

Related U.S. Application Data

[63] Continuation of Ser. No. 635,008, Dec. 28, 1990, abandoned.

[51] Int. Cl.$^5$ .............................................. A61M 5/00
[52] U.S. Cl. ..................................... 604/110; 604/218
[58] Field of Search ............... 604/110, 187, 218, 220, 604/221, 228

[56] References Cited

U.S. PATENT DOCUMENTS

| | | | |
|---|---|---|---|
| 4,391,272 | 7/1983 | Staempfli | 604/110 |
| 4,775,364 | 10/1988 | Ales | 604/110 |
| 4,863,427 | 9/1989 | Cocchi | 604/110 |
| 4,929,231 | 5/1990 | Pawlikowski | 604/221 |
| 4,932,941 | 6/1990 | Min et al. | 604/110 |
| 4,950,243 | 8/1990 | Estruch | 604/218 X |

*Primary Examiner*—John D. Yasko
*Attorney, Agent, or Firm*—Eugene J. A. Gierczak

[57] ABSTRACT

A non-reusable hypodermic syringe is provided which comprises an elongated cylinder open at one end and substantially closed at the opposite other end. A hollow member is formed on the other end, which hollow end defines an internal duct communicating with the interior of the cylinder. The hollow member is configured and dimensioned to have a hypodermic needle affixed to it. The syringe plunger is comprised of a substantially rigid shaft and a resilient piston releasably attached to a first end of the shaft member. The piston fits into the interior of the cylinder in longitudinally sliding, frictional sealing engagement therewith. An engagement member is positioned on the piston member, and a retention member is positioned on the interior wall of the cylinder adjacent to, but spaced from the other end of the cylinder. The retention member projects into the interior of the cylinder so as to define a terminal end zone of the cylinder between the closed end and the retention member, and is configured and dimensioned to cooperate with the piston and the engagement member to allow insertion of the piston into the terminal end zone upon urging by the shaft in a first longitudinal direction toward the closed end and to blockingly engage the engagement member upon retraction of the shaft in a second opposite longitudinal direction so as to cause release of the piston from the shaft and retention of the piston within the terminal end zone upon continued retraction of the shaft.

8 Claims, 2 Drawing Sheets

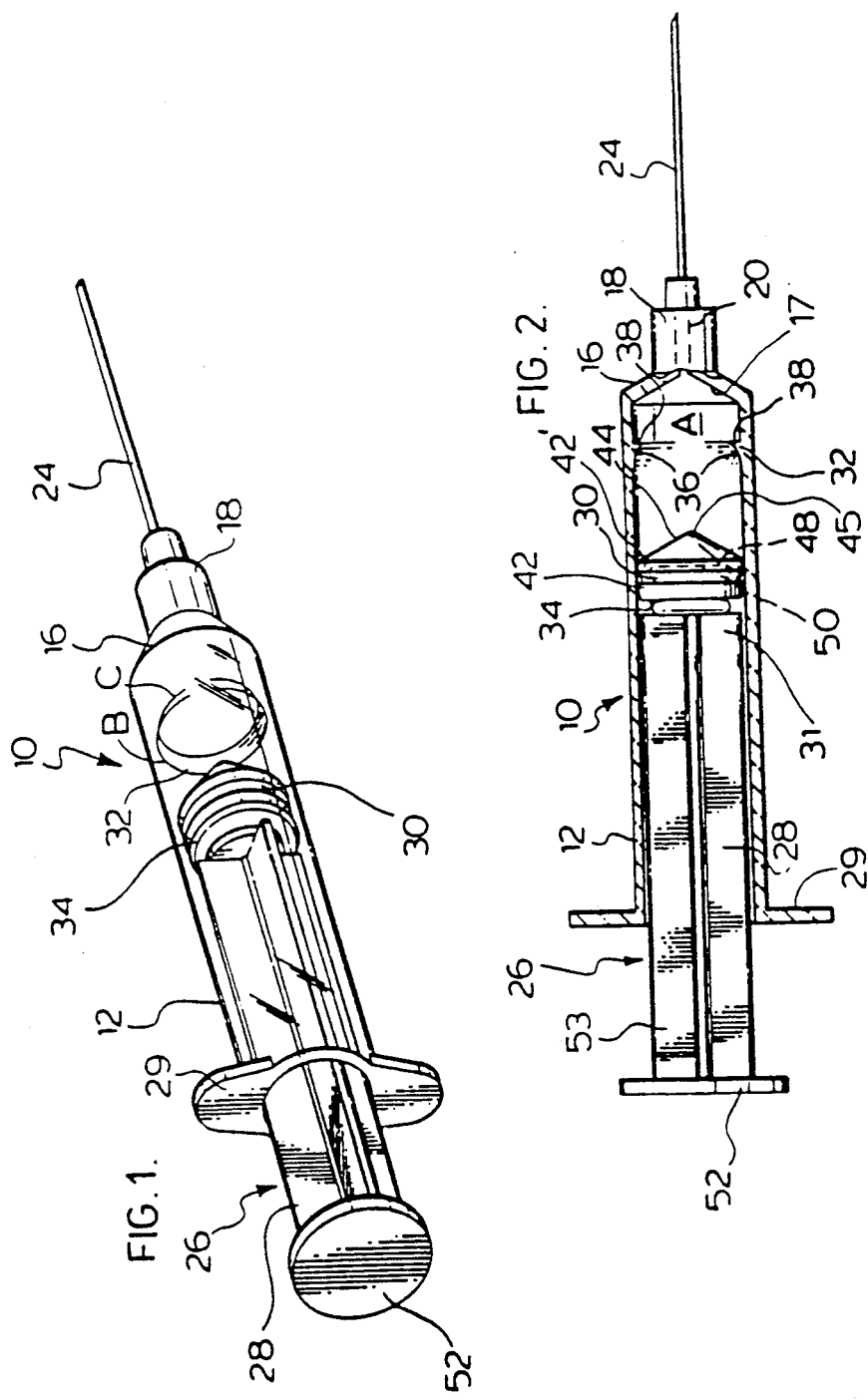

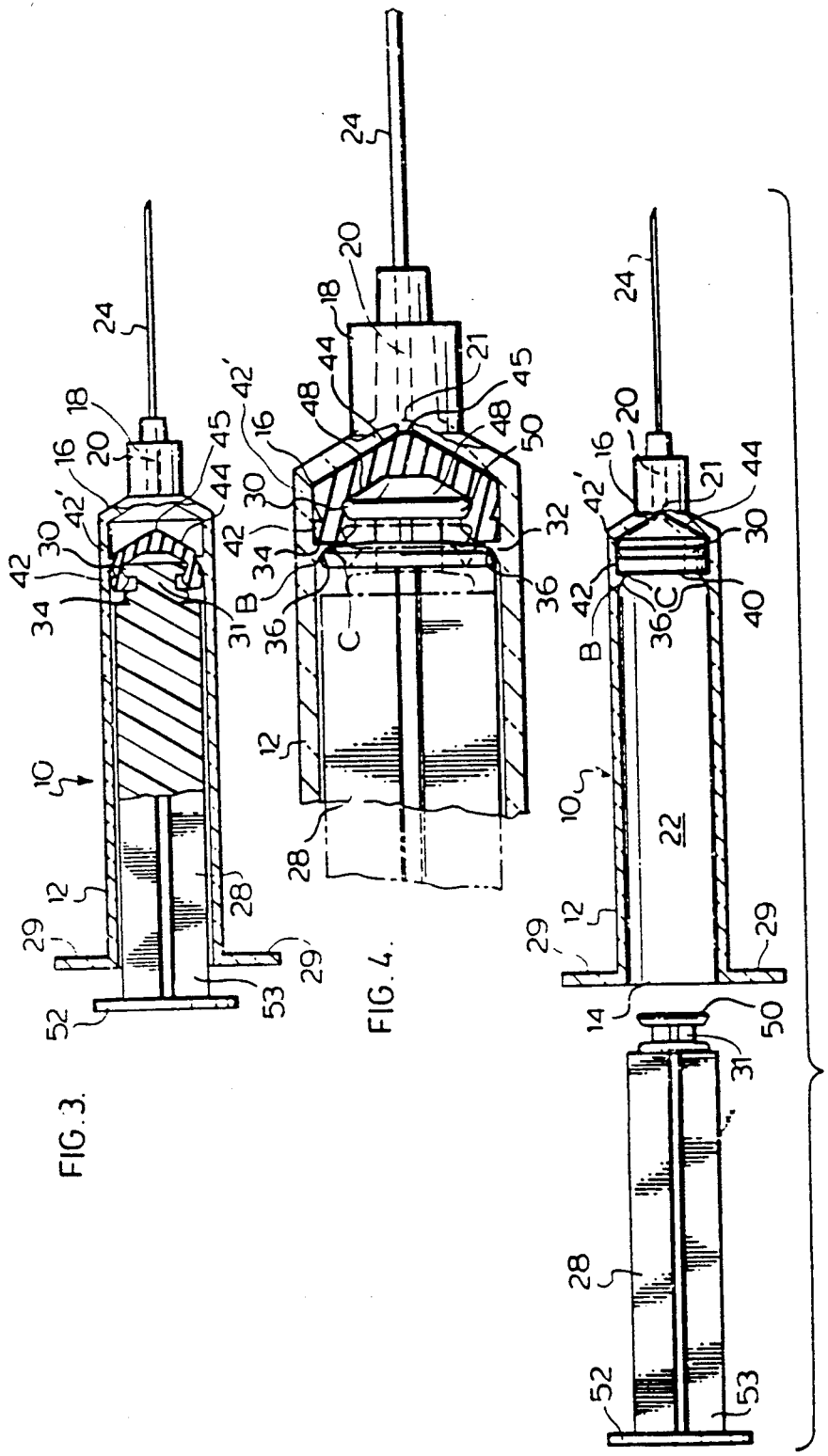

SINGLE USE SYRINGE

This is a continuation of application Ser. No. 07/635,008 filed Dec. 28, 1990, now abandoned.

FIELD OF THE INVENTION

The present invention relates to a single use syringe that is rendered inoperative after a single injection without requiring any deliberate action on the part of the user.

BACKGROUND OF THE INVENTION

In conventional syringes, including those intended to be disposable after a single usage, it is mechanically possible to re-load and discharge the instrument repeatedly. Such re-use of syringes has been identified as a source for spreading blood-transmitted infectious agents, including hepatitis viruses and the human immunodeficiency virus (HIV), which is believed to play a role in the causation of acquired immunodeficiency syndrome (AIDS).

Various health agencies, including the World Health Organization, have recently expressed an interest in the development of an inexpensive, non-reusable syringe to prevent patient-to-patient HIV transmission, particularly in the third world or other development countries.

While the prior art teaches numerous syringe designs having means for rendering them inoperable after a single use, none of these designs has seen widespread acceptance or use by the medical community. An important reason for such non-acceptance stems from the readily apparent complexity of previously proposed single-use designs. See, for example, Canadian Patent No. 872,929 (Solowey). Such complexity not only adds to the cost of producing the syringes, but also makes them unreliable and detracts from the simplicity of use which the medical community expects and demands. The increased cost factor is especially important in relation to the developing countries, where the spread of HIV is particularly threatening.

Some prior art syringes, in an attempt to achieve non-reusability, enlarge a portion of the inside diameter of the syringe barrel so as to provide a retention means for on the inside of the syringe barrel to be engaged by an engagement member associated with the piston member. In doing this, however, such syringes impair the sealing integrity between the piston member and the internal wall of the syringe barrel.

The majority of the prior art single-use syringe designs require some action to be taken by the medical staff using them to render them inoperable. For example, U.S. Pat. No. 4,790,822 (Haining) requires the user to withdraw the plunger to retract the hypodermic needle into the syringe barrel and to snap off the plunger shaft to prevent the needle from becoming re-exposed. Public health researchers have found that medical staff, particularly in third world countries, are not taking the action necessary to render such prior art syringes inoperative. Accordingly, passive inactivation of the syringe is desirable. That is, to be effective and accepted by the medical community at large, a single-use syringe must be rendered inoperative without requiring any deliberate action (e.g., withdrawal of the plunger and breaking of the hypodermic needle) on the part of the user. The user in such instance is not required to depart from familiar procedures which he/she has become accustomed to over many years.

SUMMARY OF THE INVENTION

The present invention relates to a single use syringe which overcomes the deficiencies of prior art single use syringes by providing a non-reusable syringe which is inexpensive to produce, requiring only minimal changes to already existing production equipment and molds. Moreover, maintaining a substantially constant inside diameter along substantially the whole length of the syringe cylinder ensures sealing integrity along such length. Additionally, packaging for the novel syringe disclosed herein remains unchanged from that used with conventionally available syringes, and, perhaps most importantly, the single use syringe of the invention does not require any significant changes to presently accepted methods of syringe use utilized by the medical profession.

There is thus disclosed according to the present invention a non-reusable hypodermic syringe comprising an elongated cylinder open at one end and substantially closed at the opposite other end. A hollow member is attached to the closed end and defines an internal duct communicating with the interior of the cylinder, the hollow member being configured and dimensioned in the usual manner to have a hypodermic needle affixed to it. A plunger means comprised of a substantially rigid shaft member and a resilient piston member is releasably attached to one end of the shaft member, the piston member fitting into the interior of the cylinder in longitudinally sliding, frictional sealing engagement with the cylinder. An engagement member is positioned on the piston member. A retention means is positioned on the interior wall of the cylinder adjacent to, but spaced from the other end of the cylinder. The retention means projects into the interior of the cylinder so as to define a terminal end zone of the cylinder between the other end of the cylinder and the retention means. The retention means is configured and dimensioned to cooperate with the piston member and the engagement member to allow insertion of the piston member into the terminal end zone upon urging by the shaft member in a first longitudinal direction toward the other end of the cylinder, and to blockingly engage the engagement member upon retraction of the shaft member in a second opposite longitudinal direction so as to cause release of the piston member from the shaft member and retention of the piston member within the terminal end zone upon continued retraction of the shaft member. Preferably, the retention means is comprised of an inwardly inclined, annular ramped portion of decreasing inside diameter toward the other end of the cylinder, and the ramped portion reaches a minimum inside diameter and terminates at an outwardly stepped annular wall portion. The plane defined by the annular wall portion is arranged, for maximum blocking effect, substantially transverse to the axis of the cylinder.

The engagement member, for maximum simplicity, is ideally comprised of the trailing face of the piston member, which trailing face is substantially planar and of greater outside diameter than the aforesaid inside diameter of the retention means. The plane defined by the trailing face of the piston member is oriented substantially transverse to the axis of the cylinder.

The materials used in the construction of the syringe of the invention are conventional, with the cylinder and the shaft member being formed from substantially rigid plastics materials, and the piston member being formed from natural or synthetic rubber materials which are conventionally used and well known in the art.

BRIEF DESCRIPTION OF THE DRAWINGS

FIG. 1 of the drawings is a side perspective view of a preferred embodiment of non-reusable hypodermic syringe according to the present invention in its approximate initial configuration.

FIG. 2 of the drawings is a side elevational view of the syringe of FIG. 1, shown partly in cross section, and illustrating the device in the same configuration as shown in FIG. 1.

FIG. 3 of the drawings is a view similar to FIG. 2, with the syringe in an intermediate configuration explained more fully below.

FIG. 4 of the drawings is a view of a portion of the syringe of FIG. 3, with the syringe in a fully inserted configuration as explained more fully below.

FIG. 5 of the drawings is a side elevational view, partly in section, of the syringe of the previous Figures, showing the shaft member fully retracted so as to render the syringe non-reusable.

DETAILED DESCRIPTION OF A PREFERRED EMBODIMENT OF THE INVENTION

Referring now to the Figures, there will be seen a non-reusable hypodermic syringe 10 having an elongated cylinder 12 open at one end 14 and substantially closed at the opposite other end 16. A hollow member 18 is integrally formed on said other end 16 and defines an internal duct 20 communicating with the interior 22 of the cylinder 12. The axis of the internal duct 20 is substantially aligned with the axis of the cylinder. The hollow member 18 is configured and dimensioned to accept a standard hypodermic needle 24 in releasable frictionally engaged relation, with the duct 20 in communication with the lumen (not shown) of the needle 24. The cylinder 12 and the hollow member 18 are preferably integrally moulded of a substantially rigid plastics material, such as polyethylene. As thus far described under this heading, the components of the hypodermic syringe of the invention are conventional in terms of materials, dimensions and construction, which are well-known in the art.

A plunger means 26 is provided, which plunger means 26 is comprised of a substantially rigid shaft member 28 and a resilient piston member 30 releasably attached to a first end 31 of the shaft member 28. The piston member 30 is dimensioned and adapted to fit into the interior 22 of the cylinder 12 in longitudinally sliding, frictional sealing engagement therewith.

The piston member 30 shown is of generally conventional design, preferably having two substantially parallel sealing ring members 42, 42', integrally formed on the circumference of the piston member 30 at opposite axial ends thereof in generally transverse planar orientation to the axis of the cylinder 12. The sealing ring members 42, 42' preferably have flattened outer edges (as illustrated) for effecting said frictional sealing engagement between the piston member 30 and the interior wall 23 of the cylinder 12, although any other conventional ring profiles may be used, so long as they effectively seal against fluid leakage in use. The leading face 44 of the piston member 30 is shaped to present a generally frusto-conical profile, such that its apex 45 is substantially aligned with the axis of the cylinder 12 when inserted into the cylinder 12. The inside wall 17 of the other end 16 of the cylinder 12 is formed with a complimentary frusto-conical profile to facilitate mating with the leading face 44 of the piston member 30 when fully inserted into the cylinder 12, thereby to substantially discharge liquid from the interior of the cylinder. Such full discharge is also facilitated by the alignment and mating of the apex 45 of the leading face 44 with the interior opening of the proximal end 21 of the internal duct 20 upon said full insertion of the piston member 30.

One of the ring members 42' is preferably positioned on the piston member 30 adjacent to the leading face 44 and the other 42 of the sealing ring members is preferably positioned on the piston member adjacent to a generally planar trailing face 40 of the piston member 30, the plane defined by said trailing face 40 being oriented substantially transverse to the axis of the cylinder 12 with the piston member 30 inserted in the cylinder 12.

The piston member 30 may be integrally moulded in a conventional manner from a resilient natural or synthetic rubber material, as is well known in the art, and the outside diameter of the sealing ring members 42, 42' are preferably slightly oversize of the internal diameter of the cylinder 12, so as to facilitate the aforementioned longitudinally sliding, frictional sealing engagement therewith.

The shaft member 28 is preferably of cruciform cross-section and may be constructed of any substantially rigid plastics material conventionally used for this purpose. A first end 31 of the shaft member 28 is formed with a disc-shaped portion 50, the plane of which is disc-shaped portion 50 is generally transverse to the axis of the shaft. The disc-shaped portion 50 is dimensioned to be releasably fitted into a recessed socket portion 48 centrally formed below and opening onto the trailing face 40 of the piston member 30. The socket portion 48 is dimensioned to releasably receive the disc-shaped portion 50 of the shaft member 28 in releasable resilient frictional engagement, as will be described in more detail below, with particular reference to FIG. 4. A second end 53 of the shaft member 28 opposed to said first end 31 is formed with an enlarged disc-shaped handle portion 52 adapted for gripping by a user during use of the syringe 10. The remainder of the shaft member 28 is of substantially conventional design, except as noted further below.

An engagement member 34, which, in the preferred embodiment illustrated, comprises the trailing face 40 of the piston member 30, is positioned on and integrally formed with the piston member 30. The trailing face 40 is, as described above, substantially planar, and the outer circumferential edge of the trailing face 40 preferably joins the trailing sealing ring member 42 at substantially right angles. The trailing face 40 is of substantially greater outside diameter than the aforementioned inside diameter of the retention means 32, so as to be effectively blockingly engaged by the retention means 32 upon retraction of the shaft member from the syringe 10 as will be described more fully below.

A retention means, designated by the general reference numeral 32, is positioned on the interior wall 23 of the cylinder 12, adjacent to, but spaced from, the other end 16 of the cylinder 12. The retention means 32 projects into the interior 22 of the cylinder 12, so as to define a terminal end zone of the cylinder 12 between the inside wall 17 of the other end 16 and the retention means 32. This terminal end zone is indicated by reference letter "A" in FIG. 2. In the preferred embodiment illustrated, the retention means 32 is comprised of an inwardly inclined, annular ramped portion 36 of decreasing inside diameter toward said other end 16. The ramped portion 36, which preferably has a generally parabolic slope, starts at a point "B" of maximum inside diameter coincident with the inside diameter of the cylinder 12 and reaches a minimum inside diameter at point "C", which point "C" marks the outer edge of an outwardly stepped generally planar annular wall portion 38. The plane defined by the annular wall portion 38 is arranged, as will be apparent from the Figures, substantially transverse to the axis of the cylinder 12. By utilizing a smooth gently curved ramped portion 36, followed at point "C" by an abrupt outwardly stepped annular wall portion 38, the retention means 32 is configured and dimensioned to cooperate with the piston member 30 and the engagement member 34 to allow insertion of the piston member into the terminal end zone "A" upon urging by the shaft member 28 in the first longitudinal direction toward the closed end 16 of the cylinder 12 by providing for a gradual and equal compression of the piston member 30 and engagement member 34, while at the same time allowing for the blocking engagement of the trailing face 40 of the piston member 30 upon retraction of the shaft member 28 in the second opposite longitudinal direction, which blocking is facilitated by the full expansion of the piston member 30 and engagement member 34 within the terminal end zone "A".

As previously mentioned, it is preferable that the outside diameters of both sealing ring members 42 and 42' be slightly larger than the inside diameter of the cylinder 12, so as to facilitate sealing of the piston member 12 with the interior wall 23 of the cylinder. As will be apparent from the Figures, this requirement for sealing with the interior wall 23 means that both sealing ring members 42, 42' are necessarily of greater outside diameter than the minimum inside diameter of the annular ramped portion 36 of the retention means 32. However, it is preferable for smooth operation of the preferred syringe embodiment illustrated that the trailing sealing ring member 42 be of slightly greater outside diameter than that of the leading sealing ring member 42'. The desirability of this relative sizing of the sealing ring members 42, 42' will become apparent from the description of the operation of the illustrated syringe of the invention which follows.

Usage of the preferred embodiment of non-reusable syringe 12 shown in the Figures will now be described in relation to a typical patient injection of, for example, a liquid antibiotic, so as to explain the general manner of operation of the invention. It will be appreciated by those skilled in the art that other operations utilizing a hypodermic syringe, for example, drawing blood from a patient, can be carried out in an analogous manner, with minor variances from the injection procedure described.

FIGS. 1 and 2 of the drawings show a preferred embodiment of a non-reusable syringe according to the invention in its initial configuration after removal from the sterile packaging in which it would be received by a user and prior to it being used. In this initial configuration, the shaft member 28 is attached to the piston member 30, and the plunger means 26 is only partially inserted into the interior 22 of the cylinder 12, so that the leading face 44 of the piston member 30 is outside of the terminal end zone "A". In carrying out an injection, the user takes the syringe 10 in this initial configuration, inverts the bottle or vial (not shown) of antibiotic or other medicament to be injected, and inserts the needle 24 through the rubber stopper or other closure of the bottle or vial. Once fluid contact with the liquid contents of the bottle or vial has been made through such insertion of the needle 24, the user then grips the handle portion 52 on the second end of the shaft member 28 and retracts the shaft member 28 (with the attached piston member 30) an intermediate distance in a second longitudinal direction, i.e., toward the open end 14 of the cylinder, until a sufficient quantity of liquid has been drawn from the bottle or vial into the interior 22 of the cylinder 12 the between leading face 44 of the piston member 30 and the inside wall 17 of the closed end 16 of the cylinder 12. The needle 24 is then withdrawn by the user from the stopper by way of force in the second longitudinal direction exerted by the user on the integral gripping ears 29,29 positioned on the cylinder 12 adjacent its open end 14. With the syringe 10 still inverted, the shaft member 28 (with the attached piston member 30) is then urged by the user in a first longitudinal direction, i.e., towards the closed other end 16 of the cylinder 12, so as to expel air and any excess liquid from the interior 22 of the cylinder 12. In this step, the user should avoid allowing the piston member 30 to move fully into the terminal end zone "A", as such movement will prevent subsequent retraction of the piston means 30, as more fully described below. However, as will be appreciated from the Figures, and especially FIGS. 4 and 5, that the terminal end zone "A" has substantially the same longitudinal dimension as the piston member 30, so that such subsequent retraction will only be prevented when substantially all of the liquid has been expelled from the interior 22 of the cylinder 12.

Once the intended injection aliquot is obtained in this manner with the assistance of conventional measurement markings (not shown) on the outside of the cylinder 12, the needle 24 is then inserted into the patient in the usual manner, and the shaft member 28 (with the attached piston member 30) is again urged in the first longitudinal direction toward the closed other end 16 of the cylinder 12. During such urging, in the first longitudinal direction, the piston member 30 reaches the intermediate position shown in FIG. 3. In this position, it will be seen that the leading sealing ring member 42' has slid up the ramped portion 36 and past the annular wall portion 42 into the terminal end zone "A". However, because the outside diameter of the leading sealing ring member 42' is preferably slightly smaller than that of the trailing sealing ring member 42, it would, in the preferred embodiment illustrated, be possible to retract the piston member 30 from the terminal end zone "A" by pulling the shaft member 28 in the second longitudinal direction without causing the release of the piston member 30 from the shaft member 28. Continued urging of the shaft member 28 in the first longitudinal direction by the user causes the remainder of the piston member 30, including the trailing sealing ring member 42 (which constitutes the engagement member 36), to slide smoothly up and past the ramped portion 36 of the retention means 32, so that the piston member 30 completely enters the terminal end zone "A" and thereby assumes the fully inserted configuration shown in FIG. 4, at which configuration the piston member 30 has resiliently expanded and is thereby prevented from further sliding movement in the first longitudinal direction by contact of the leading face 44 with the inside wall 17 of the closed other end 16 of the cylinder 12. The dimensioning and smooth profiling of the ramped portion 36 have thus, in the manner described, cooperated with the natural resiliency of the piston member 30 and the engagement member 34 to facilitate smooth movement of the piston member 30 into the terminal end zone "A" by urging of the shaft member 28 in the first longitudinal direction. It will be appreciated that sealing integrity between the piston member 30 and the interior wall 23 of the cylinder 12 has been maintained during the described longitudinal movement in the first direction, and that substantially all of the injection liquid has been discharged from the cylinder 12 into the patient when the piston member 30 reaches the fully inserted configuration shown in FIG. 4.

The next step in injection usage is to remove the needle 24 and the attached syringe 12 from the patient, with the plunger means 26 still in the fully inserted configuration shown in FIG. 3. This involves no change in standard practice, as has been the case thus far in the described injection procedure.

The user may, at this point in the procedure simply discard the syringe 12 in the usual manner, as it has by full movement of the plunger means 30 into the terminal end zone "A" been rendered non-reusable. The user may retract the shaft member 28 in the second longitudinal direction by pulling on the handle portion 52 with one hand while holding the ears 29,29 with the other hand, thereby causing release of the piston member 30 from the shaft member 28 and retention of the piston member 30 within the terminal end zone "A" as described below. This extra step will assure the user of the non-reusability of the syringe 12, but release of the piston member 30 as described will occur, in any event, if subsequent re-use of the syringe 12 is attempted.

FIG. 4 illustrates in phantom outline the release of the piston member 30 from the shaft member 28. As the shaft member 28 is moved in the second longitudinal direction, the trailing face 40 of the engagement member 34 blockingly engages the planar wall portion 38 of the retention means 32. Continued movement of the shaft member 28 in the second longitudinal direction causes the disc-shaped portion 50 to release from the socket portion 48. This occurs as the resiliency of the piston member 30 allows an overlying peripheral portion 51 of the planar trailing face 40 surrounding the socket portion 48 to stretch outwardly, as shown in phantom outline in FIG. 4, and thereafter the disc-shaped portion 50 pulls completely free of the piston member 30. FIG. 5 shows the shaft member 28 fully released from the piston member 30. While the shaft member 28 can be re-inserted into the piston member 30, any attempt to withdraw the shaft member 28 will have the same releasing result, as the piston member 30 has been rendered unremovable from the terminal end zone "A", except by destructive measures. Thus, the syringe 12 of FIG. 5 has been rendered non-reusable.

In designing the non-reusable syringe 12 of the invention disclosed herein, it will be apparent that the dimensions of the various frictionally interacting components, for example, the recessed socket portion 48, the disc-shaped portion 50, the sealing ring members 42, 42' and the retention means 32, must be carefully calibrated to reliably achieve the desired frictional release of the piston member 30, while at the same time ensuring acceptable sealing performance with the interior wall 23 of the cylinder 12. Such calibration is a matter of routine experimentation for those skilled in the art, and must, be separately performed for each different size of syringe to which this invention is applied. It will also be apparent that the piston support disc 54 adjacent the first end 30 of the shaft member 28 should be dimensioned so as not to interfere in operation with the ramped portion 36 of the retention means 32, while at the same time providing adequate support to the trailing face 40 of the piston member 30.

The foregoing description of the invention has been directed to a particular preferred embodiment of the present invention for the purpose of explanation and illustration only. It will be apparent to those skilled in the art that numerous modifications and changes in the apparatus may be made without departing from the spirit and scope of the invention. For example, the profile of the retention means 32, particularly that of the ramped portion 36 can be changed significantly from that shown in the drawings without losing its intended functionality. While there are limits to such profile changes, these are easily determinable through routine experiment. Additionally, the hypodermic needle 24 may be rigidly affixed to the hollow member 18 by means of glue, swaging or other means, which is also known to the syringe art, and is particularly suited to single use applications. It is, therefore, intended that the following claims cover all equivalent modifications and variations as fall within the scope of the invention as defined in the claims appended hereto.

We claim:

1. A non-reusable hypodermic syringe, comprising:
   (a) an elongated cylinder open at one end and substantially closed at the opposite other end;
   (b) a hollow member formed on said other and defining an internal duct communicating with the interior of said cylinder, said hollow member being configured and dimensioned to have a hypodermic needle affixed to it;
   (c) a plunger means comprised of a rigid shaft member and a resilient piston member releasably attached to a first end of the shaft member, the piston member fitting into the interior of said cylinder in longitudinally sliding, frictional sealing engagement therewith;
   (d) a retention means positioned on the interior wall of the cylinder adjacent to but spaced from said other end and projecting into the interior of the cylinder so as to define a terminal end zone of the cylinder between said other end and said retention means said retention means being comprised of a continuous, inwardly inclined, annular ramp portion having a generally parabolic slope, of increasing inside diameter towards the other end, said ramped portion reaching a minimum inside diameter and terminating at an outwardly stepped generally planar annular wall portion, the plane defined by said annular wall portion being arranged substantially transverse to the axis of the said cylinder;
   (e) an engagement member comprised of the trailing face of the piston member, which trailing face is substantially planar and of greater outside diameter than said minimum inside diameter of the retention means, the plane defined by said trailing face being oriented substantially transverse to the axis of the cylinder;
whereby, the retention means is configured and dimensioned to cooperate with the piston member and the engagement member to allow insertion of the piston member into said terminal end zone upon urging by the shaft member in a first longitudinal direction towards said other end, so that said piston member completely enters said terminal zone and is thereby prevented from further sliding movement in said longitudinal direction and to blockingly engage the engagement member upon retraction of the shaft member in a second opposite longitudinal direction so as to cause release of the piston member from the shaft member and retention of the piston member within the terminal end zone upon continued retraction of the shaft member.

2. The syringe as claimed in claim 1, wherein the longitudinally sliding, frictional sealing engagement between the piston member and the interior of the cylinder is effected by means of two substantially parallel sealing ring members formed on the circumference of the piston member at opposite axial ends thereof in generally transverse planar orientation to the axis of the cylinder wherein one of said sealing ring members is positioned adjacent the leading face of said piston member and the other of said sealing ring members is positioned adjacent the trailing face of said piston member wherein said one of said sealing rings is smaller in diameter than said other of said sealing rings so as to permit retraction of said piston member from said terminal end zone without causing release of said piston member from said shaft when only said one of said sealing rings is in said terminal end zone.

3. The syringe as claimed in claim 2, wherein the longitudinally sliding, frictional sealing engagement between the piston member and the interior of the cylinder is effected by means of two substantially parallel sealing ring member formed on the circumference of the piston member at opposite axial ends thereof in generally transverse planar orientation to the axis of the cylinder.

4. The syringe as claimed in claim 3, wherein one of said sealing ring members is positioned adjacent the leading face of said piston member and the other of said sealing ring members is positioned adjacent the trailing face of said piston member.

5. The syringe as claimed in claim 4 wherein the axis of said internal duct is substantially aligned with the axis of the cylinder, and the leading face of said piston member is substantially frusto-conical, having its apex substantially aligned with the axis of the cylinder.

6. The syringe as claimed in claim 5, wherein said resilient piston member is releasably attached to the shaft member by means of a recessed socket portion centrally formed below and opening onto the trailing face of the piston member, which socket portion is dimensioned to releasably receive in resilient retaining frictional engagement a disc-shaped portion formed on said first end of the shaft member.

7. The syringe as claimed in claim 5, wherein the piston member is constructed from a resilient natural or synthetic rubber material.

8. The syringe as claimed in claim 7, wherein a second end of the shaft member opposed to said first end is formed with a handle portion adapted for gripping by a user of the syringe.

* * * * *